(12) United States Patent
Ormsby

(10) Patent No.: US 8,133,222 B2
(45) Date of Patent: Mar. 13, 2012

(54) TISSUE ABLATION APPARATUS AND METHOD USING ULTRASONIC IMAGING

(75) Inventor: Theodore C. Ormsby, Escondido, CA (US)

(73) Assignee: Medwaves, Inc., San Diego, CA (US)

(*) Notice: Subject to any disclaimer, the term of this patent is extended or adjusted under 35 U.S.C. 154(b) by 886 days.

(21) Appl. No.: 12/128,530

(22) Filed: May 28, 2008

(65) Prior Publication Data

US 2009/0299360 A1 Dec. 3, 2009

(51) Int. Cl.
*A61B 18/14* (2006.01)

(52) U.S. Cl. .......................... 606/41; 600/439

(58) Field of Classification Search .................... 606/41; 600/439

See application file for complete search history.

(56) References Cited

U.S. PATENT DOCUMENTS

| | | |
|---|---|---|
| 3,309,455 A | 3/1967 | Mildner |
| 4,408,089 A | 10/1983 | Nixon |
| 4,583,556 A | 4/1986 | Hines et al. |
| 4,776,086 A | 10/1988 | Kasevich |
| 4,841,977 A * | 6/1989 | Griffith et al. ............... 600/439 |
| 5,150,717 A | 9/1992 | Rosen et al. |
| 5,370,644 A | 12/1994 | Langberg |
| 5,385,148 A | 1/1995 | Lesh et al. |
| 5,462,521 A | 10/1995 | Brucker et al. |
| 5,496,271 A | 3/1996 | Burton et al. |
| 5,500,012 A | 3/1996 | Brucker et al. |
| 5,542,916 A * | 8/1996 | Hirsch et al. .................. 604/22 |
| 5,545,193 A | 8/1996 | Fleischman et al. |
| 5,575,766 A | 11/1996 | Swartz et al. |
| 5,656,028 A | 8/1997 | Swartz et al. |
| 5,656,029 A | 8/1997 | Miran et al. |
| 5,656,796 A | 8/1997 | Marinos et al. |
| 5,683,382 A | 11/1997 | Lenihan et al. |
| 5,690,611 A | 11/1997 | Swartz et al. |
| 5,702,433 A | 12/1997 | Taylor et al. |
| 5,707,349 A | 1/1998 | Edwards |
| 5,722,400 A | 3/1998 | Ockuly et al. |

(Continued)

FOREIGN PATENT DOCUMENTS

EP 1055399 11/2000

(Continued)

OTHER PUBLICATIONS

International Search Report and Written Opinion issued in corresponding PCT/US2009/044406 on Jan. 6, 2010.

(Continued)

*Primary Examiner* — Michael Peffley
*Assistant Examiner* — Daniel Fowler
(74) *Attorney, Agent, or Firm* — Procopio, Cory, Hargreaves & Savitch LLP

(57) ABSTRACT

A coaxial cable apparatus which transmits radio frequency (RF) energy for the ablation of biological tissues has inner and outer coaxial conductors extending from a proximal portion to a distal portion. An RF antenna is disposed at the distal portion of the cable and transmits RF energy for ablation of a tissue region to be treated. At least one ultrasonic transducer is also disposed at the distal portion of the cable to direct ultrasonic frequency energy to a tissue region. The ultrasonic transducer detects reflected ultrasonic signals from the tissue region and provides a signal output which varies dependent on the density of tissue over the monitored tissue region. The reflected ultrasonic signal can be monitored before, during, and after ablation treatment.

27 Claims, 9 Drawing Sheets

U.S. PATENT DOCUMENTS

| | | |
|---|---|---|
| 5,730,719 A | 3/1998 | Edwards |
| 5,738,114 A | 4/1998 | Edwards |
| 5,738,683 A | 4/1998 | Osypka |
| 5,741,249 A | 4/1998 | Moss et al. |
| 5,743,870 A | 4/1998 | Edwards |
| 5,755,754 A | 5/1998 | Rudie et al. |
| 5,776,176 A | 7/1998 | Rudie |
| 5,785,706 A | 7/1998 | Bednarek |
| 5,800,379 A | 9/1998 | Edwards |
| 5,800,429 A | 9/1998 | Edwards |
| 5,800,482 A | 9/1998 | Pomeranz et al. |
| 5,800,494 A | 9/1998 | Campbell et al. |
| 5,814,027 A | 9/1998 | Hassett et al. |
| 5,817,049 A | 10/1998 | Edwards |
| 5,820,580 A | 10/1998 | Edwards et al. |
| 5,824,005 A | 10/1998 | Motamedi et al. |
| 5,836,906 A | 11/1998 | Edwards |
| 5,837,001 A | 11/1998 | Mackey |
| 5,842,984 A | 12/1998 | Avitall |
| 5,849,028 A | 12/1998 | Chen et al. |
| 5,853,368 A | 12/1998 | Solomon et al. |
| 5,863,291 A | 1/1999 | Schaer |
| 5,885,278 A | 3/1999 | Fleischman |
| 5,897,554 A | 4/1999 | Chia et al. |
| 5,921,982 A * | 7/1999 | Lesh et al. ............... 606/41 |
| 5,957,969 A | 9/1999 | Warner et al. |
| 5,964,755 A | 10/1999 | Edwards |
| 5,971,983 A | 10/1999 | Lesh |
| 6,004,269 A * | 12/1999 | Crowley et al. ............ 600/439 |
| 6,012,457 A | 1/2000 | Lesh |
| 6,014,579 A | 1/2000 | Pomeranz et al. |
| 6,032,077 A | 2/2000 | Pomeranz |
| 6,161,543 A | 12/2000 | Cox et al. |
| 6,164,283 A | 12/2000 | Lesh |
| 6,190,382 B1 | 2/2001 | Ormsby et al. |
| 6,228,076 B1 | 5/2001 | Winston et al. |
| 6,245,064 B1 | 6/2001 | Lesh et al. |
| 6,254,599 B1 | 7/2001 | Lesh et al. |
| 6,355,033 B1 | 3/2002 | Moorman et al. |
| 6,383,182 B1 | 5/2002 | Berube et al. |
| 6,416,511 B1 | 7/2002 | Lesh et al. |
| 6,584,360 B2 | 6/2003 | Francischelli et al. |
| 6,595,989 B1 | 7/2003 | Schaer |
| 6,618,620 B1 | 9/2003 | Freundlich et al. |
| 6,643,535 B2 | 11/2003 | Damasco et al. |
| 6,652,515 B1 | 11/2003 | Maguire et al. |
| 6,663,625 B1 | 12/2003 | Ormsby et al. |
| 6,669,693 B2 | 12/2003 | Friedman |
| 6,673,068 B1 | 1/2004 | Berube |
| 6,694,170 B1 | 2/2004 | Mikus et al. |
| 6,702,811 B2 | 3/2004 | Stewart et al. |
| 6,711,429 B1 | 3/2004 | Gilboa et al. |
| 6,758,830 B1 | 7/2004 | Schaer et al. |
| 6,811,544 B2 | 11/2004 | Schaer |
| 6,814,730 B2 | 11/2004 | Li |
| 6,849,075 B2 | 2/2005 | Bertolero et al. |
| 6,878,149 B2 | 4/2005 | Gatto |
| 6,887,238 B2 | 5/2005 | Jahns et al. |
| 6,958,062 B1 | 10/2005 | Gough et al. |
| 6,997,925 B2 | 2/2006 | Maguire et al. |
| 7,004,938 B2 | 2/2006 | Ormsby et al. |
| 7,070,595 B2 | 7/2006 | Ormsby et al. |
| 7,769,469 B2 * | 8/2010 | Carr et al. ............... 607/101 |
| 2003/0171672 A1 | 9/2003 | Varghese et al. |
| 2004/0116921 A1 | 6/2004 | Sherman et al. |
| 2004/0267252 A1 | 12/2004 | Washington et al. |
| 2006/0142752 A1 | 6/2006 | Ormsby et al. |
| 2006/0287649 A1 | 12/2006 | Ormsby et al. |
| 2007/0066972 A1 | 3/2007 | Ormsby et al. |
| 2007/0185554 A1 | 8/2007 | Appling et al. |
| 2008/0015570 A1 | 1/2008 | Ormsby et al. |
| 2008/0108867 A1 | 5/2008 | Zhou |

FOREIGN PATENT DOCUMENTS

| | | |
|---|---|---|
| EP | 1554986 | 7/2005 |
| WO | 97/26544 | 7/1997 |
| WO | 02/26146 | 4/2002 |
| WO | 03022167 | 3/2003 |
| WO | 2006086152 | 8/2006 |

OTHER PUBLICATIONS

Communication dated Aug. 25, 2011 and extended European Search Report dated Aug. 16, 2011 for EP 09767227, 7 pages.

* cited by examiner

TISSUE ABLATION APPARATUS AND METHOD USING ULTRASONIC IMAGING

BACKGROUND

1. Field of the Invention

The present invention generally relates to medical devices which are used for the irradiation of biological tissues, such as devices for the ablation of biological tissues, and more particularly to a radio frequency energy transmission system for such devices which uses ultrasonic imaging for tissue mapping.

2. Related Art

Therapeutic tissue ablation systems apply energy to a biological ablation tissue site via different energy exchange means, such as heat conduction and irradiation. These systems may employ various energy modes, such as radiofrequency, ultrasound, laser, cryogenic, and the like. Within the radio frequency (RF) range, certain microwave ablation systems are used to destroy or ablate biological tissues. In one application, a microwave ablation system is used to ablate cardiac tissues that cause irregular heartbeats or arrhythmia, avoiding the need for more risky and invasive open heart surgery. In such an application, an ablation member such as an RF antenna is incorporated as part of a catheter. The catheter is passed through the vein for access to the atrium. Within the atrium, the RF antenna is positioned at the desired location where ablation is applied.

Microwave ablation systems can also be used in treatment of other biological sites such as arteries, organs and body vessels. As an example, a microwave ablation system is used to ablate tumors in the lungs, liver, kidney or other areas of the body.

These surgical and therapeutic applications require an efficient system for the transmission of radio frequency energy to the ablating member for the delivery of energy to the target tissue site, and also require accurate location of the tissue site to be ablated. Prior art ablation catheters have been equipped with two or more electrocardiogram ("ECG") electrodes to provide the necessary output signal for identification of the desired ablation site. It is also known to use ultrasound to provide detailed imaging of the area of interest, by positioning both an ultrasound imaging catheter and a separate ablation catheter at the site of interest. However, it is difficult to maneuver both catheters simultaneously in the limited space available in order to perform ablation therapy while imaging the area using the ultrasound imaging catheter.

SUMMARY

The present invention provides an innovative radio frequency energy transmission system and method for the ablation of biological tissues in body areas such as the heart, liver, and the like. The embodiments described herein provide a conductive hollow coaxial cable device with one or more ultrasonic transducers for detecting the density contrast of tissue in the vicinity of the device.

In one embodiment, a tissue ablation or treatment system comprises a hollow conductive coaxial cable device for placement adjacent to or within biological tissues, the cable device having a proximal end and a distal end and having inner and outer conductors which extend along at least part of the length of the cable up to a distal portion of the cable, an ablating member such as an RF antenna at the distal portion of the cable for the ablation of the tissue, and at least one ultrasonic transducer at the distal portion of the cable for detecting the density contrast of the biological tissue load. In one embodiment, the ultrasonic transducer is connected via one of the inner and outer conductors and an additional lead to a suitable power supply and to an output or receiver device which interprets the reflected ultrasonic signal received by the transducer in a known manner in order to map tissue density in a monitored region. This avoids the need to provide completely separate wiring for the RF antenna and the ultrasonic transducer.

In one embodiment, the ablating member comprises a radio frequency transmitter or antenna, which may be a helical coil or a monopole, having one end connected to the inner conductive member and a second end connected to the outer conductive member. A radio frequency signal generator is connected to the coaxial cable device to generate a train of RF pulses along the cable to the RF antenna, along with a controller or control unit for adjusting the RF signal according to predetermined parameters. In one embodiment, the radio frequency may be a microwave frequency from approximately 300 MHz and up. An ultrasonic drive signal generator is also connected to provide power to the ultrasonic transducer.

In one embodiment, a dielectric medium is selectively disposed between the inner and outer conductors. The dielectric medium may comprise a solid or a fluid material, or a combination of both, and may assume alternative structure features.

A plurality of ultrasonic transducers or sensors may be provided in an array at the distal portion of the coaxial cable device in one embodiment. A single array of ultrasonic transducers or multiple arrays may be provided, so as to allow mapping of larger tissue areas.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide for a radio frequency energy transmission device, which incorporates a coaxial cable for conducting radio frequency (RF) energy, particularly microwave energy, for the ablation of biological tissues. The cable has coaxial inner and outer conductors which extend up to a distal portion of the cable. The inner conductor has an elongated electrically conductive tubular member with a hollow, axially extending lumen. The outer conductor has an elongated electrically conductive tubular member, which is arranged in a substantially coaxial relationship over the inner conductor. A dielectric medium is selectively disposed between the inner and outer conductors. An ablating member which delivers radio frequency energy, particularly microwave energy, is located at the distal portion of the cable, along with one or more ultrasonic transducers for tissue density imaging purposes.

After reading this description, it will become apparent to one skilled in the art how to implement the invention in various alternative embodiments and alternative applications. However, although various embodiments of the present invention will be described herein, it is understood that these embodiments are presented by way of example only and not limitation. As such, this detailed description of various alternative embodiments should not be construed to limit the scope or breadth of the present invention as set forth in the appended claims.

Figure 1:
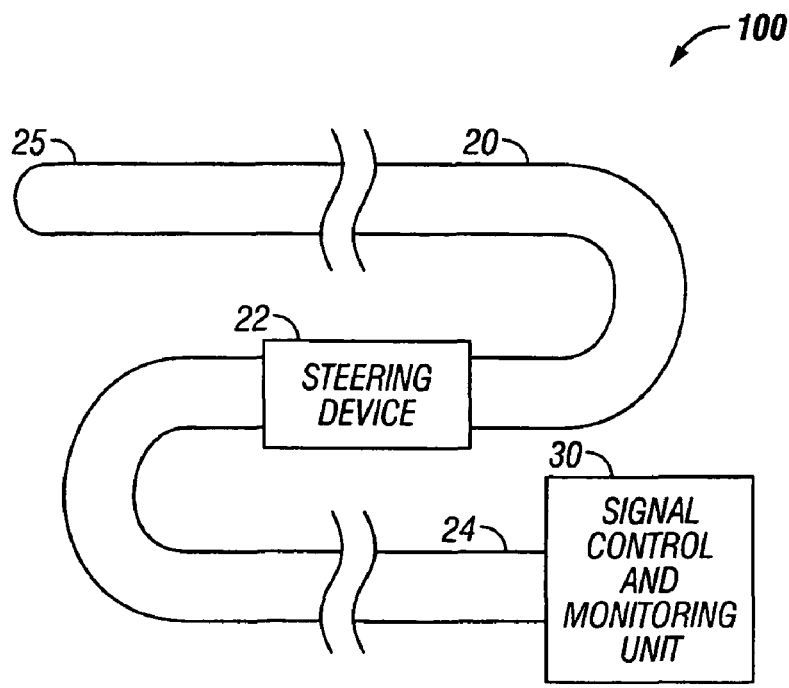
FIG. 1 is a schematic block diagram, partly broken away, of one embodiment of a tissue ablation system.

FIG. 1 illustrates a radio frequency energy transmission (RF) energy ablation system 100, which comprises an elongated coaxial cable apparatus or device 20 adapted for placement adjacent to or within a biological tissue site and/or a body vessel of a patient, a handle and steering unit 22 positioned at the proximal end of the cable device 20, and a signal control and monitoring unit 30 coupled with the proximal end of the coaxial cable device via cable 24. The handle unit 22 contains steering and positioning controls (not illustrated) for the coaxial cable device. The signal control and monitoring unit 30 is described in more detail below in connection with FIG. 12.

The distal portion 25 of one embodiment of the coaxial cable apparatus is illustrated in FIGS. 2A to 2E, and incorporates an ablation device 26, such as an RF antenna, for delivering electromagnetic energy to the treatment site, as well as an ultrasonic sensor assembly 28 for monitoring tissue density in an area of the tissue to be treated prior to, during, and after a tissue ablation procedure, as described in more detail below.

An RF signal generator in control unit 30 is electrically coupled to the ablation device 26 through the coaxial cable, as described in more detail below. The RF signal generator and control unit for controlling the RF signal delivered to the ablation device may be similar to that described in the pending application Ser. No. 11/479,259 filed on Jun. 30, 2006, the contents of which are incorporated herein by reference.

The length and diameters of coaxial cable device 20 are adapted as required to suit the particular medical procedure, as is known in the medical art. Coaxial device 20 is generally tubular and has a multi-layer construction with a central bore or lumen 34 extending along its length. The distal end 35 of the lumen 24 may be closed as illustrated in FIG. 2 or it may be open in other embodiments, for example as described and shown in U.S. Pat. No. 6,663,625, the contents of which are incorporated herein by reference.

Figure 2A:
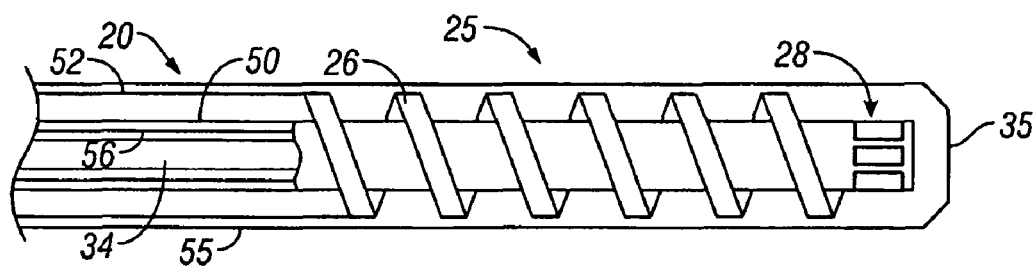
FIG. 2A is a schematically simplified side elevation view, partially broken away, of the distal portion of a first embodiment of the hollow conductive coaxial cable device of the system of FIG. 1, incorporating an ultrasonic transducer array.
Figure 2B:
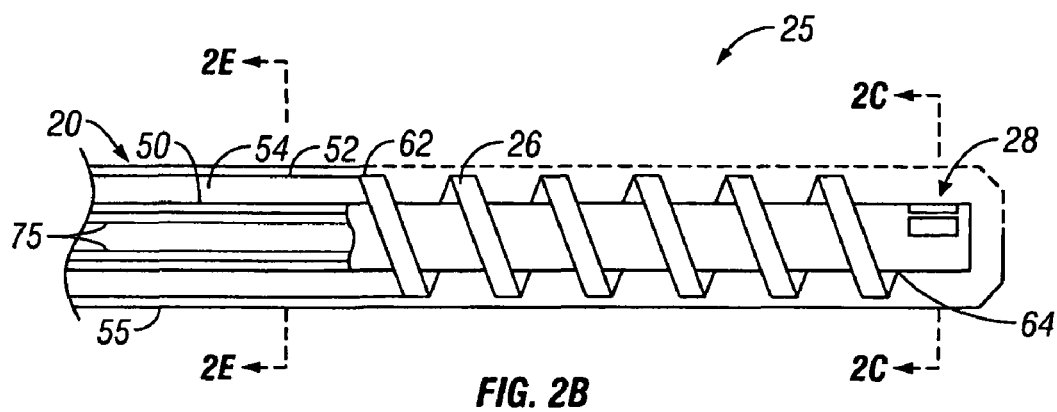
FIG. 2B is a schematically simplified view of the distal portion, similar to FIG. 2A but rotated through ninety degrees.
Figure 2C:
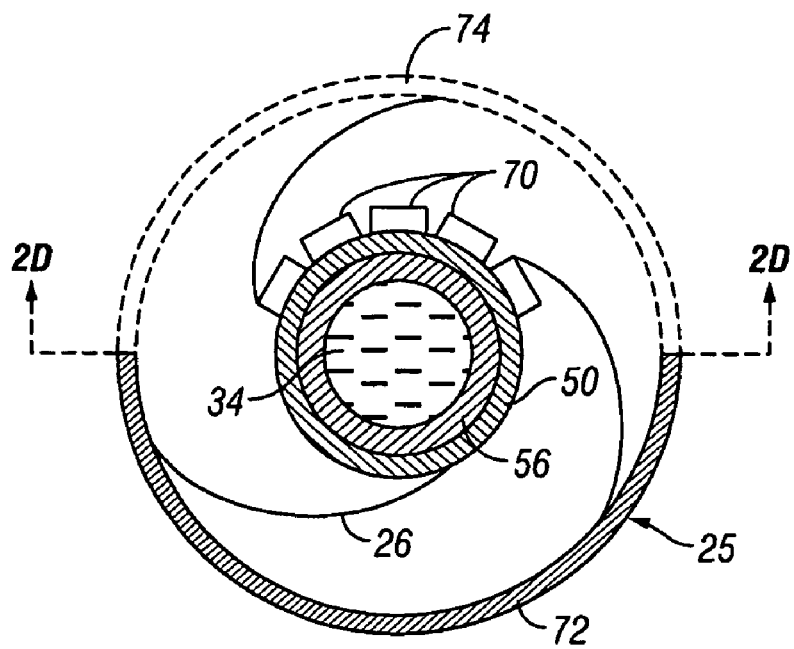
FIG. 2C is a detailed cross-sectional view through the distal portion of the cable device of FIGS. 2A and 2B, taken on the lines 2C-2C of FIG. 2B.
Figure 2D:
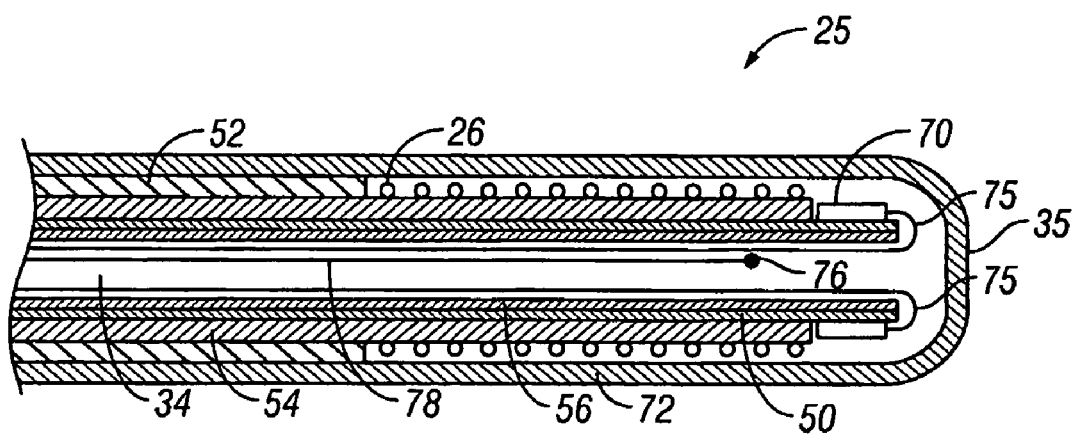
FIG. 2D is a cross sectional view on the lines 2D-2D of FIG. 2C, illustrating the ultrasonic transducers and connecting leads to the transducers in more detail.
Figure 2E:
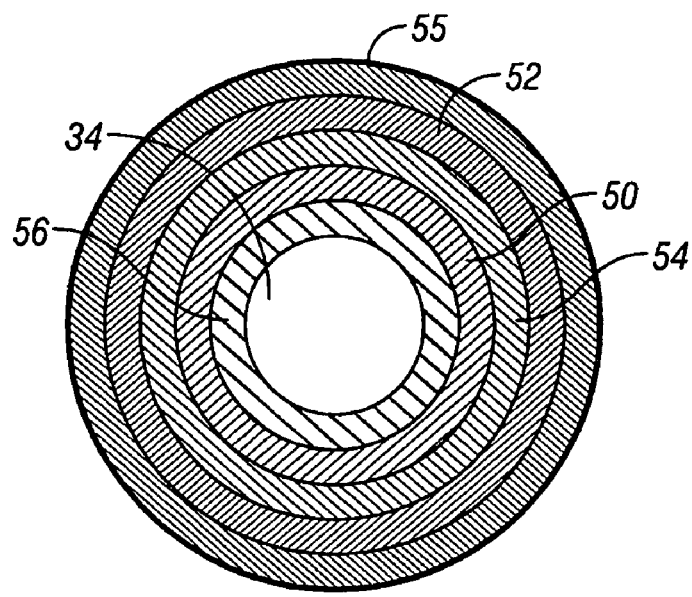
FIG. 2E is a cross sectional view on the lines 2E-2E of FIG. 2B.

As illustrated in FIGS. 2A to 2E, the coaxial cable apparatus 20 has a first or inner electrically conductive tubular member or conductor 50 having a proximal end portion and a distal end portion, and a second or outer electrically conductive tubular member 52 extending coaxially with the inner conductor along the majority of the length of device 20 but terminating at the distal portion 25. FIGS. 2A and 2B are simplified schematic views of the distal portion 25 of the device, partially in cross-section but with various components shown as single lines for simplicity, for ease in illustrating the ultrasonic sensor assembly and other components. FIGS. 2C to 2E are more detailed sectional views to show the layered structure of the device 20 including distal portion 25. The inner and outer conductors may extend along substantially the entire length of the cable from the proximal end up to the distal portion 25. In an alternative embodiment, conductors 50, 52 may extend along only part of the cable up to the distal portion 25.

Inner conductor 50 and outer conductor 52 each comprise an elongated electrically conductive tubular member, with outer conductor 52 arranged in a substantially coaxial relationship over at least a portion of length of the inner conductor 50. This arrangement defines an annular space between the walls of the inner conductor 50 and the outer conductor 52 which is filled with a layer 54 of dielectric material. An outer jacket or casing 55 of dielectric polymer material encloses the co-axial conductors 50, 52 and extends to the tip of the device 20. An inner liner or support tube 56 of flexible dielectric material extends within the inner conductor 50 up to a location close to the distal end or tip of the device 20 and surrounds the hollow central bore or lumen 34. In one embodiment, the lumen 34 within tube 56 is filled with a microwave and ultrasound transparent dielectric material.

In this embodiment, the ablation device 26 located at the distal portion 25 of the coaxial cable apparatus 20 comprises a helical coil radio frequency (RF) antenna which is electrically coupled to both the outer coaxial conductor 52 at contact point 62 and to the inner conductor 50 at its opposite end, at contact point 64. In turn, the inner conductor and the second or outer conductor are electrically coupled to the RF energy source in unit 30. In the illustrated embodiment, the ablation device 26 comprises a helical coil wound around the outer circumferential surface of the coaxial cable device and extending from the end portion of the outer conductor 52 up to the distal end of the device 20. The helical coil 26 is coated with an outer coating layer of dielectric material (not illustrated) such as a polymeric dielectric encapsulant which protects the structural integrity of the coil and also shields it from the surrounding biological environment. In alternative embodiments, other forms of ablation devices or radio frequency antennas may be used in place of the helical coil antenna 26, such as a monopole bead antenna as illustrated in the embodiments of FIGS. 6 to 11 described in more detail below, or a pair of spaced electrically conductive microstrips disposed at the distal portion of the coaxial cable device, as described in U.S. Pat. No. 6,663,625 referenced above, the contents of which are incorporated herein by reference. The RF antenna 26 includes an electrically conductive material or wire strip that is wound in a helical fashion to form the helical coil. The appropriate diameter, pitch and length of the coil winding and the selection of the conductive material or wire strip are a matter of choice, which can vary according to the particular procedure requirements as known in the art. Thus these design elements and considerations are not detailed here.

As shown in FIGS. 2A, 2B and 2E, a dielectric medium 54 is provided in the space between tubular coaxial conductors 50 and 52 to impede electrical conduction between the inner conductor 50 and outer conductor 52. The dielectric medium is formed from a solid or a fluid or a combination of solid and fluid. Selectively, the dielectric is formed of a dielectric layer which substantially fills the space between the inner conductor 50 and outer conduction 52. Any unfilled space may be evacuated to form a vacuum or filled with an alternative dielectric solid or fluid material. A dielectric fluid medium such as air may be dispensed in lieu of the solid dielectric layer 55. Vacuum, which also exhibits dielectric property, may be introduced by the evacuation of air and sealing the space between the distal and proximal end portions of the cable during manufacture. Alternately, a vacuum source may be configured in fluid communication with the space between the inner and outer conductors in lieu of the placement of a dielectric medium as a vacuum can exhibit dielectric property.

As mentioned above, outer jacket or casing 55 encases the outer conductor 52 along the length of the coaxial cable device up to the distal portion 25. The outer casing 55 is generally constructed of a polymer material that is bio-compatible within the body vessel environment. Examples of such materials include thermoplastic elastomer material such as Pebax® available from Autochem Germany, polyethylene, polyurethane, polyester, polyimide, polyamide, and the like, with varying degrees of radiopacity, hardness, and elasticity.

The tubular body of the coaxial cable device 20 may be formed with a plurality of segments using one or more of the aforementioned materials or equivalents, such that the device 20 is progressively more flexible towards its distal end. The segments may be joined together by thermal bonding, butt joints, or adhesive bonding. Braiding reinforcement may be provided to the surface of the tubular body to attain a desirable level of stiffness and torsional strength for the device to advance and negotiate through the body vessel of the patient, while still allowing the distal end portion to be bent when needed. The distal portion 25 may be of a softer polymer compound than the remainder of the body, with little or no braiding or reinforcement, to provide the desired flexibility for distal deflection and shaping of the apparatus.

In one embodiment, inner conductor 50 and outer conductor 52 may be made of a flexible braided wire construction or thin film electrically conductive material or the like. The inner liner or tube 56 and the inner conductor 50 extend from handle unit 40 through the distal portion of the coaxial cable device, while the outer conductor 52 and dielectric layer 54 extend from the handle unit 40 and terminate short of the distal portion of the device. In one embodiment, the interior of the entire distal portion 25 of the device is filled with a microwave and ultrasound transparent dielectric material which surrounds the helical coil antenna 26. The material may be fluid or solid.

In this embodiment, the ultrasonic sensor assembly 28 comprises a semi-circular array of ultrasonic sensors or transducers 70 spaced around the half of the circumference of inner conductor 50 adjacent its distal end, as best illustrated in FIGS. 2C and 2D. The sensors or transducers 70 are positioned to direct ultrasonic signals radially outwardly from the microwave antenna, and to receive echo signals reflected from tissue in the field of view of the transducers. The outer casing 55 at the distal portion 25 of coaxial cable or microwave ablation device 20 is formed with one half segment 72 of microwave absorbing or shielding dielectric material, and one half segment 74 which surrounds the ultrasonic sensor array 28 formed of microwave and ultrasound transparent dielectric material, as indicated by the dotted line portion in FIGS. 2B and 2C. This arrangement provides a directional, 180 degree microwave and ultrasound aperture. Ultrasonic signals are directed through the microwave and ultrasound transparent portion 74 of the casing surrounding the ultrasonic transducer array 28, covering a tissue area of 180 degrees surrounding the distal end portion of the device 20. The device may be rotated to provide 360 degree imaging of the tissue surrounding the device. Although multiple ultrasonic transducers are used in the illustrated embodiments, a single transducer may be used in alternative embodiments, and may direct ultrasonic signals radially or axially. Additionally, smaller microwave and ultrasound apertures providing a field of view of less than 180 degrees may be used in other embodiments, with a corresponding reduced number of ultrasonic transducers, or smaller transducers, if more precise directional imaging and treatment beams are required. In other embodiments, one or more ultrasonic transducers may be positioned to direct ultrasonic signals axially forward from the distal end of the device, corresponding to the forwardly directed portion of the RF field. Axially directed transducers may be used alone or in conjunction with radially directed transducers as described in any of the embodiments herein.

In the embodiment of FIGS. 2A to 2E, the ultrasonic transducers 70 are connected to a drive signal generator in the signal control unit 30 at the proximal end of device 20 via a first transducer wire or lead which comprises the inner conductor 50 of the coaxial cable device, and second transducer wires or leads 75 which are connected to the outer ends of the respective ultrasonic transducers 70 as illustrated in FIG. 2D. The second transducer wires 75 extend from the respective transducers through the central lumen 34 of device 20 to the proximal end of the device, where they are connected through cable 24 to the signal control and monitoring unit 30.

The ultrasonic transducers 70 may be made of any suitable piezoelectric material such as ceramic and may have a polymeric base coated with a suitable conductor such as gold, platinum or silver which is bonded to the outer surface of the inner conductor 50 adjacent its distal tip, as best illustrated in FIGS. 2C and 2D. In one embodiment, the range of ultrasound frequency used may be of the order of 4 MHz to 40 MHz.

The RF antenna 26 is adapted to receive and radiate electromagnetic energy from a source of radio frequency energy in unit 30. An example of suitable spectrum of radio frequency is that of the microwave frequency ranging from approximately 300 MHz and up. The RF antenna imparts substantially uniformly distributed electromagnetic field energy transmitted by the helical coil. The power of the electromagnetic field transmitted is substantially normal to the longitudinal axis of the RF antenna, and a uniform energy field is produced through the semicircular aperture formed by microwave transparent window 74. The energy delivered for the ablation is substantially uniformly distributed along the antenna through the window 74, which is independent of the contact between the antenna and the tissue to be ablated.

As illustrated in FIG. 2D, a temperature sensor 76 may also be located in lumen 34 adjacent the distal end 35 of device 20, and is connected to the signal power and monitoring unit 30 via wires 78. This allows RF energy delivered to the targeted biological tissue to be optimized by controlling both the reflected power (reverse power) to the antenna and the detected tissue temperature, as described in more detail in co-pending application Ser. No. 11/479,259, the contents of which are incorporated herein by reference in their entirety. In some applications, electrocardiagram (EKG) electrodes may also be incorporated in the distal end portion of the cable apparatus.

In one embodiment, the ultrasonic array 28 is used to determine the tissue density contrast of a target tissue site prior to treatment, during treatment, and after treatment is complete. The device illustrated in FIGS. 2A to 2E has a 180 degree window, and prior to treatment the distal portion 25 may be rotated to allow mapping of the surrounding tissue. A tumor cell, for example, has a different density from other cells, and such cells can be located based on mapping of the reflected ultrasound signals which travel at different velocities which can be correlated to the density of the tissue through which they pass. The direction and intensity of the microwave beam can be adjusted based on the tissue density map at the target site during treatment. Following treatment, a further scan can be made to see whether the treatment was effective or more treatment is required.

Figure 12:
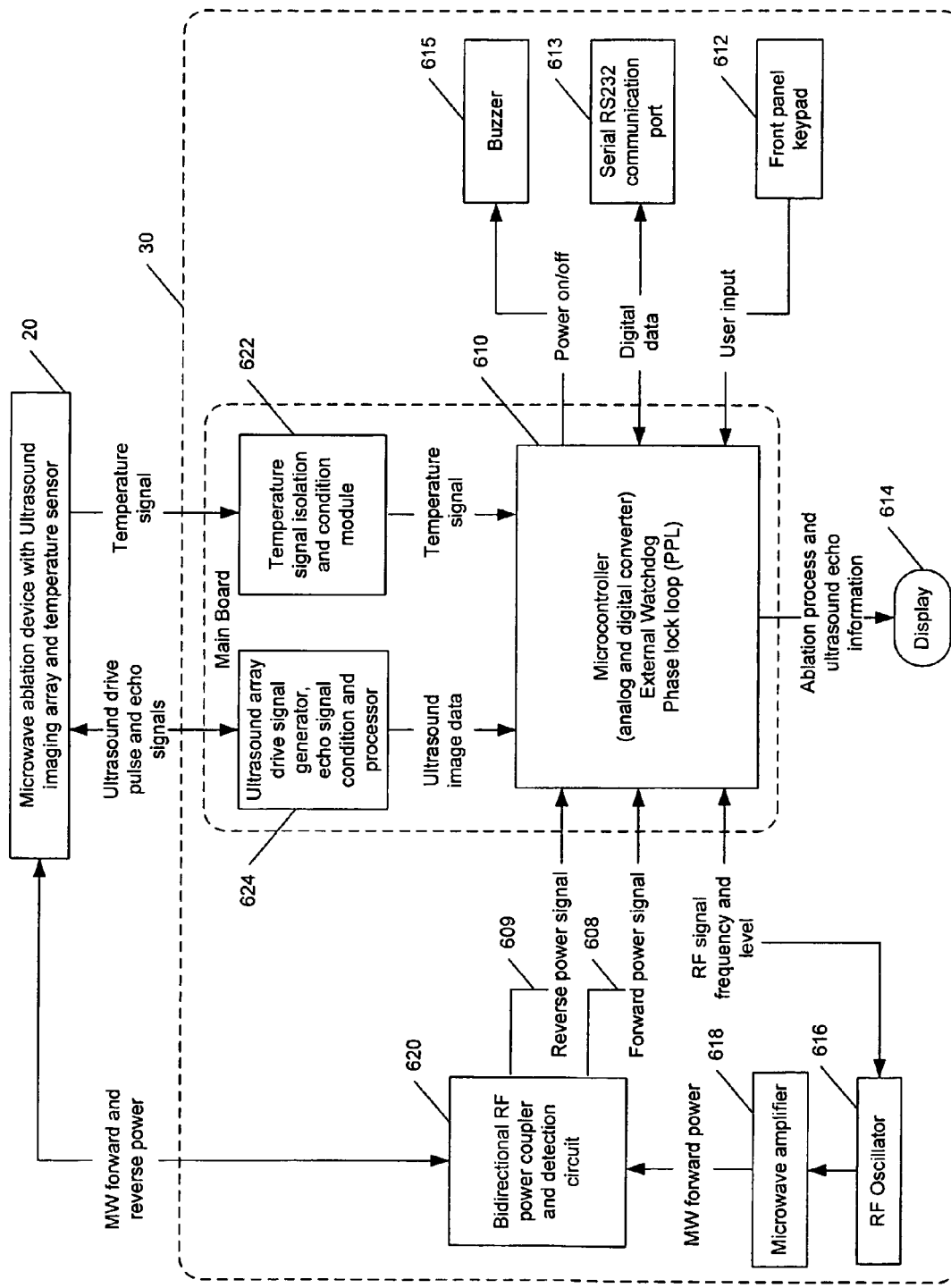
FIG. 12 is a schematic block diagram of the signal monitoring and control unit of FIG. 1 which is connected to any one of the coaxial-cable devices of FIGS. 2 to 11.

FIG. 12 illustrates the signal control and monitoring assembly or system 30 in more detail. As illustrated, unit or system 30 monitors and controls reflected/forward power ratio of the RF signal, power output, ultrasound array drive signals and sensor or ultrasound echo output signals, and temperature in the RF ablation catheter apparatus 20. System 30 has a power supply (not illustrated) which supplies power to various components of the system, and includes a microcontroller 610 for controlling operation of the system according to programmed instructions and operator input at control input 612. A display module 614 and output alarm module 615 are connected to appropriate outputs of microcontroller 610. A data output port 613 is also provided to connect the output to other remote devices. Display module 614 provides an output display of the status of the ablation process as well as the ultrasound tissue mapping or echo signal information.

Microcontroller 610 is also connected to an RF signal generator or oscillator 616, which may be a phase-locked loop (PLL) oscillator. The RF signal oscillator 616 is connected to power amplifier 618, which includes a preamplifier for initially amplifying the output signal from RF oscillator 616, and a second RF amplifier for final amplification of the signal. After amplification by the RF amplifier 618, the pulsed RF signal is delivered through bi-directional coupler 620 to the RF transmission line of the ablation device 20. The bi-directional coupler 620 samples the relatively low energy forward pulses transmitted along the transmission line to the RF antenna 26 and the energy pulses reflected back from the target ablation tissue, and provides the forward and reflected pulse samples as feedback signals 608, 609 to the microcontroller 610. A temperature signal detect and condition module 622 is connected to the temperature signal conductors 78 at the end of RF transmission line 560, and the temperature signal output of module 622 is also connected to microcontroller 610.

Ultrasound array drive signal generator module 624 is connected via first and second ultrasound transducer leads 50, 75 to the ultrasound transducers 70 in the tip of the ablation device or coaxial cable device 20. In the embodiment of FIGS. 2A to 2E, the transducer leads comprise the inner conductor 50 of the coaxial cable device, and the wires 75 which extend from the outer end of each transducer through the lumen 34 of device 20. Module 624 also includes ultrasound echo signal conditioning and processing devices, and produces ultrasound image data connected to the microcontroller 610.

The microcontroller is programmed to monitor the power output and the forward and reflected energy pulses, and to compute the ratio between the forward and reflected energy pulses, or the voltage standing wave ratio VSWR as defined co-pending application Ser. No. 11/479,259 referenced above. Additionally, the microcontroller is also programmed to monitor the temperature detected at temperature sensor 76 which is closely related to the temperature induced in the tissue as a result of the ablation process, since the temperature sensor 76 is located close to the ablation site. Temperature sensor 76 is mounted in the lumen 34 at the distal tip of the device 20 in the illustrated embodiment, but may be mounted on the outside surface of the catheter or at other locations in the distal end portion of the catheter in alternative embodiments. The microprocessor is also programmed to monitor the ultrasound image data received from ultrasound module 624 and to provide a tissue density map for display on the output display unit 614.

In this embodiment, the microcontroller 610 is programmed to adjust the frequency to achieve a minimum reflected to forward power ratio, and to adjust the RF power level to achieve a selected temperature setting or to increase or decrease tissue ablation based on the detected output from the ultrasonic transducers. A combination of the temperature sensor output and the ultrasonic sensor output may be used to adjust the RF power level and frequency. The temperature setting may be a temperature set point, plus or minus a few degrees, or may be a selected temperature range, as described in co-pending application Ser. No. 11/479,259 referenced above. The reflected power is proportional to the combined impedance of the biological tissue and the antenna system as a whole, and therefore minimizing the reflected power is the same as impedance matching the system for maximum transfer of forward power for delivery to the tissue being ablated. At the same time, the temperature changes that are measured by the temperature sensor can be correlated to the combined RF energy effect (ablation) of the biological tissue and the antenna system as a whole. Once the set points of the temperature as measured are set, the RF frequency and the power delivered to the target tissue can be adjusted within the preset temperature set points and can also be adjusted based on tissue density determined from the ultrasonic sensor outputs in order to improve the effectiveness of a tissue ablation procedure.

Although this embodiment uses detected temperature, detected ultrasound signals, and reverse to forward power ratio as control parameters in adjusting the RF signal parameters in order to achieve a temperature and a power ratio close to user or default settings, alternative embodiments can use temperature alone or the ultrasound signals alone as the control parameter. In one embodiment, the ultrasonic sensors are used in conjunction with the temperature sensor (or sensors) in order to adjust the output frequency of the RF pulses in order to effect a substantial match of the transmission line impedance with the RF antenna and biological tissue load impedance. Alternatively, the ultrasonic sensor output alone may be used for this purpose, and the temperature sensor may be omitted in alternative embodiments. The microcontroller may also monitor the output power and temperature to ensure that they do not exceed maximum limits for safe operation. The microcontroller adjusts the RF frequency by controlling oscillator 616, thereby also adjusting the reflected/forward power ratio. RF power delivered can be adjusted up and down by controlling amplifier 618, in turn adjusting the detected temperature.

In addition to monitoring the reflected power and detected temperature as parameters for controlling the RF frequency and power delivered to the target tissue, the system is also arranged to control the signal generator module 624 for the ultrasonic array 28, and to receive ultrasound image data from the module 624 and create tissue density maps based on the image data for display on output display unit 614. Ultrasonic signals are emitted from the ultrasonic transducer area and directed radially from the transducers outo the tissue region surrounding the distal end portion 25 of the transducer. Signals reflected through the tissue are received by the transducers or sensors 70 and transmitted along inner conductor 50 and wires 75 to the ultrasound drive signal and echo signal module 624. As the ultrasonic signals travel through the tissue, portions of the signals are reflected to the sensors. The reflected signals travel at different velocities which can be correlated to the density of the tissue on which the signals are focused. The density contrast from one location to another may indicate abnormalities or other tissue characteristics. For example, tumors are generally of a higher density than healthy tissue. The ultrasonic transducer array and signal processing module 624 together form a tissue imaging system which is incorporated into the treatment head so that tissue monitoring can take place prior to treatment in order to accurately position the antenna, and also while treatment is taking place in order to adjust the ablation signal output from the antenna based on the detected ablation depth. Imaging after treatment is complete and comparison with tissue maps created prior to treatment can help to determine the effectiveness of the treatment.

In the embodiment of FIGS. 2A to 2E, the ultrasonic transducer array 28 comprises a series of transducers spaced circumferentially around half of the circumference of the inner conductor 50 adjacent its distal end, and ultrasonic energy is directed radially outwards from conductor 50 in a 180 degree range surrounding the microwave transparent portion 74 of the outer casing 55 in the distal portion 25 of device 20. In alternative embodiments, a greater or lesser number of transducers 70 may be provided and they may be located at different positions in the distal portion of device 20 spaced radially about the central axis of the antenna, or spaced axially in parallel with the antenna axis. FIGS. 3A to 11 illustrate some alternative ultrasonic transducer arrangements as well as some alternative microwave antenna arrangements. These embodiments are otherwise identical to the first embodiment and use the same signal control and monitoring unit or system as described above in connection with FIGS. 1 and 12 in order to control the RF frequency and energy directed onto a treatment site as well as to obtain tissue density maps of the treatment site prior to, during, and after treatment.

Figure 3A:
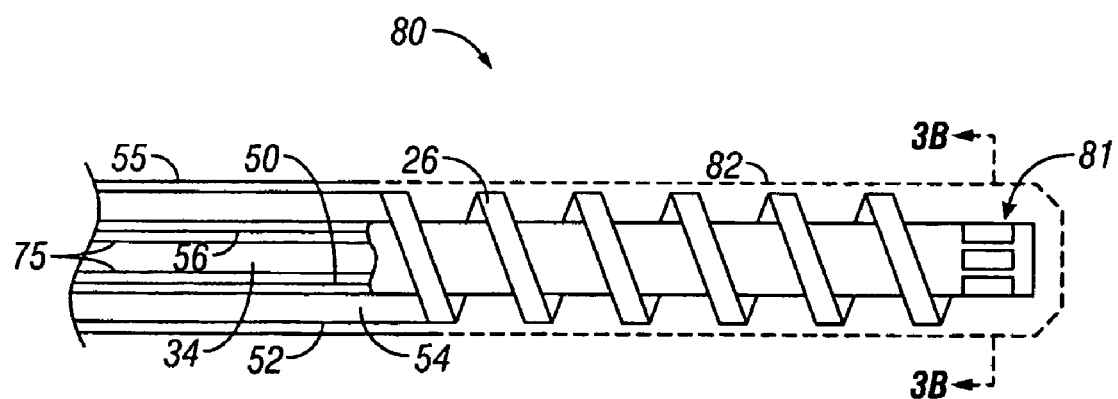
FIG. 3A is a schematically simplified view similar to FIG. 2A of the distal portion of a modified coaxial cable device with a different ultrasonic transducer and outer cover arrangement.
Figure 3B:
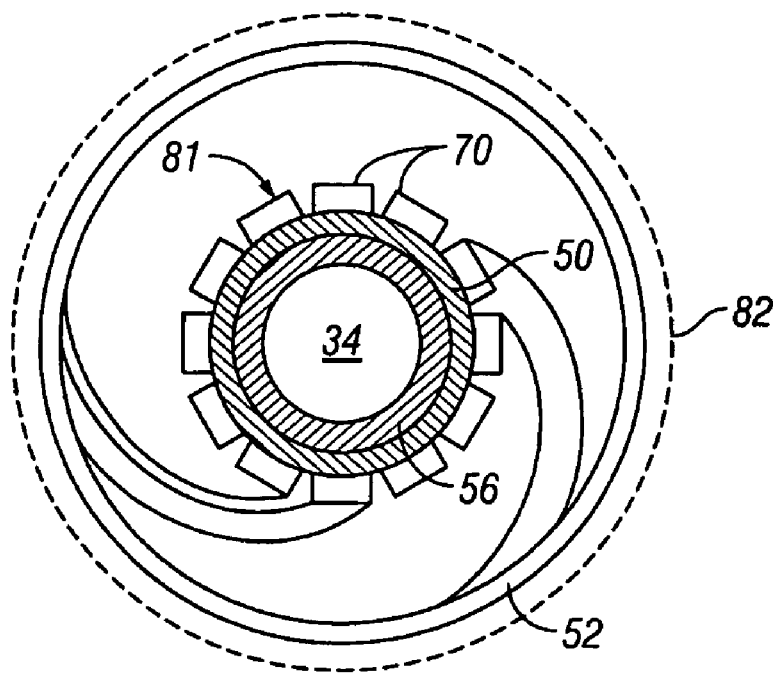
FIG. 3B is a cross-sectional view on the lines 3B-3B of FIG. 3A.

In the embodiment illustrated in FIGS. 3A and 3B, the apparatus 20 has a modified distal portion 80 in which an array 81 of spaced ultrasonic transducers 70 is provided around the entire circumference of the inner conductor 50, as illustrated in FIG. 3B. Additionally, the entire casing portion 82 surrounding the antenna 26 and transducers 70 at the distal portion of the cable is of microwave transparent material. This arrangement provides a 360 degree or omnidirectional microwave and ultrasound field aperture. As in the previous embodiment, the ultrasonic transducer elements 70 are located distal to the microwave antenna. Other parts in FIGS. 3A and 3B are identical to the previous embodiment, and like reference numbers are used for like parts as appropriate.

Figure 4:
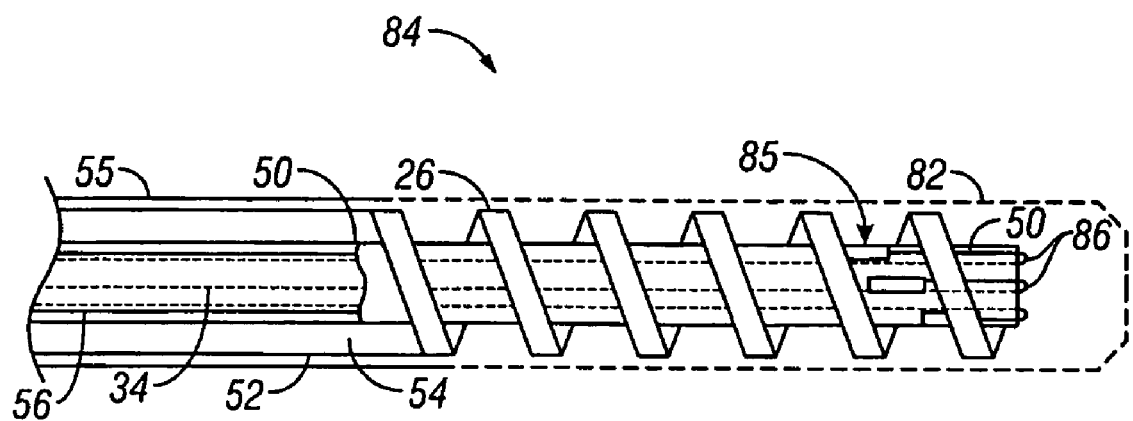
FIG. 4 is a schematically simplified view similar to FIGS. 2A and 3A but illustrating the distal portion of another modified coaxial cable device with a different ultrasonic transducer arrangement.

FIG. 4 illustrates another alternative embodiment in which the distal portion 84 of device 20 again has a 360 degree microwave and ultrasound aperture, similar to the previous embodiment, but the array 85 of ultrasound elements 70 in this case is spaced rearward and within the microwave antenna 26. The elements 70 in FIG. 4 are spaced around the entire outer circumference of the inner conductor 50, in the same way as illustrated in FIG. 3B of the previous embodiment, but in this embodiment the elements 70 are also axially staggered around the circumference of conductor 50, as seen in FIG. 4. This provides greater coverage of the surrounding tissue. Other parts in this embodiment are identical to the previous embodiments, and like reference numbers are used for like parts as appropriate. As in the previous embodiments, the inner coaxial conductor 50 provides one electrical lead from the transducer array to module 624. The second connector or lead comprises wires 86 extending through lumen 34 around the open end of conductor 50 and bending back to connect to the distal ends of the respective transducers.

Figure 5A:
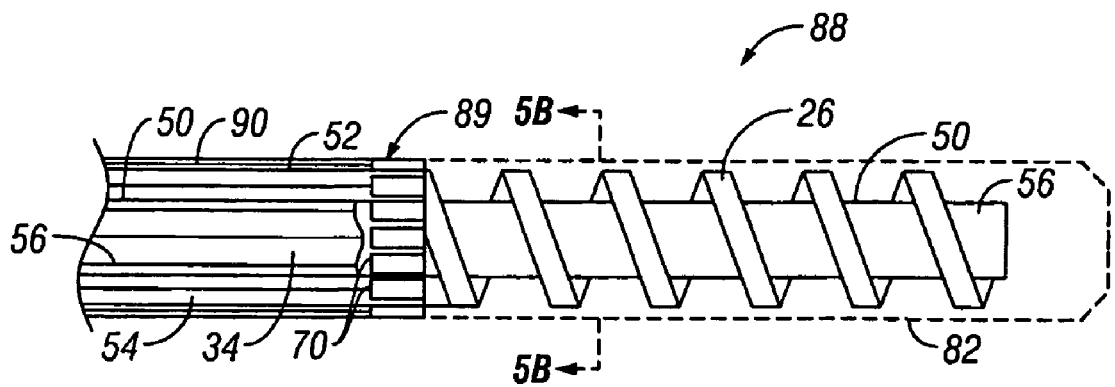
FIG. 5A is a schematical simplified view, similar to FIGS. 2A, 3A and 4, showing the distal portion of another embodiment of a coaxial cable device with a different ultrasonic transducer and outer cover arrangement.
Figure 5B:
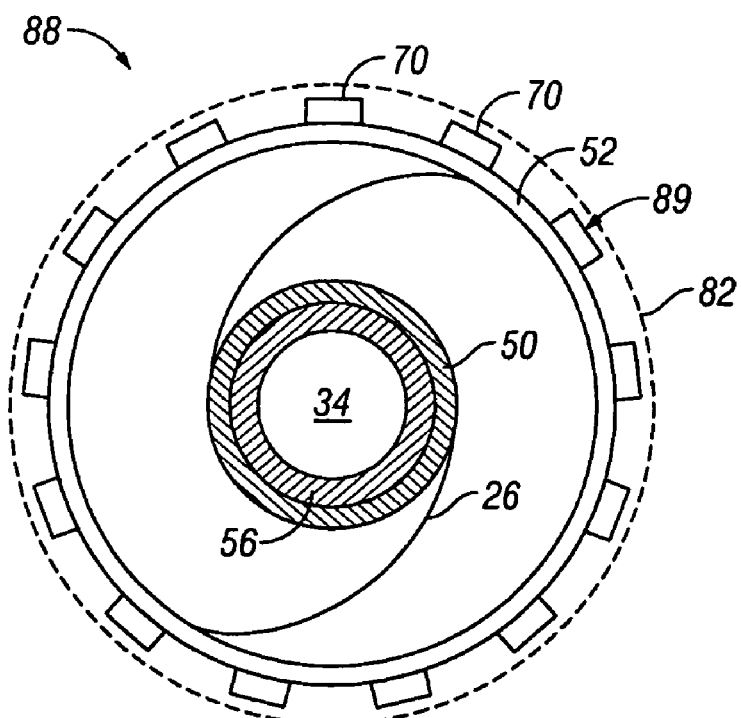
FIG. 5B is a cross-sectional view on the lines 5B-5B of FIG. 5A.

In the previous embodiments, ultrasonic transducers 70 are mounted on the outer surface of the inner conductor 50 of the coaxial cable device 20. FIGS. 5A and 5B illustrate a coaxial cable apparatus having a modified distal portion 88 in which ultrasonic transducers are instead mounted in an array 89 around the outer surface of the outer transducer 52, adjacent the proximal end of antenna 26. The individual transducers 70 may be identical to those of the previous embodiments, although positioned at a different location in the distal portion of device 20. In this case, the outer conductor 52 comprises a first lead between each transducer 70 of the array 89 and the proximal end of device 20. Wires 90 may extend over a shielding layer covering the outer conductor 52 to connect to the distal ends of transducers 88, forming the second ultrasonic transducer wires or leads for each transducer. Alternatively, wires 90 may extend through dielectric medium 54 in the space between the inner and outer conductors 50, 52 before connecting to the distal ends of transducers 88. Other parts of the device in FIGS. 5A and 5B are identical to the previous embodiments, and like reference numbers are used for like parts as appropriate.

The embodiment of FIGS. 5A and 5B again has a 360 degree or omnidirectional microwave and ultrasound signal aperture. In an alternative embodiment, a 180 degree window may be provided in a similar manner to the first embodiment, with transducers 88 spaced around only half of the outer circumference of the outer conductor 52, as is the case in some of the embodiments described below.

Figure 6:
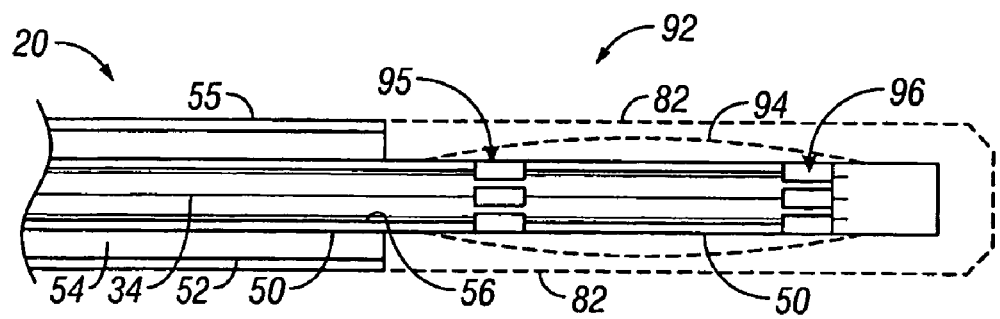
FIG. 6 is a schematically simplified view similar to FIGS. 2A, 3A and 4, but illustrating the distal portion of another embodiment of a coaxial cable device having a monopole antenna and a different ultrasonic transducer arrangement.

The following embodiments have more than one set or array of ultrasonic transducers positioned in the distal portion of a coaxial cable ablation device 20. FIG. 6 illustrates an embodiment in which the distal portion 92 of ablation device 20 has a modified RF antenna and modified ultrasonic transducer assembly. Other parts of the coaxial cable or ablation device 20 are identical to parts in one or more of the previous embodiments, and like reference numbers are used for like parts as appropriate. In this embodiment, the RF antenna is a monopole antenna which may comprise the projecting end portion of the inner conductor 50 itself, or may be a monopole bead antenna 94 as indicated in dotted line in FIG. 6. When the inner and outer conductors are energized, they act as a waveguide with an electromagnetic field generated between them, and this field propagates radially outwardly from the monopole antenna 94 or inner conductor through microwave transparent casing 82 in the distal portion 92 of the device, where it can be applied for tissue ablation purposes. Since the outer cover or casing 82 in the distal end portion is transparent to microwaves around its entire circumference, the device has a 360 degree microwave field aperture, as in the embodiments of FIGS. 3, 4 and 5.

The ultrasonic transducer assembly in this embodiment comprises two spaced sets 95, 96 of ultrasonic transducers 70, with the transducers in each set spaced around the entire circumference of the inner conductor 50, in the same way as illustrated for the single set or array 81 shown in FIG. 3B. The first set 95 of transducers is spaced forward from the distal end of the outer conductor 52, and the second set 96 is spaced forward from the first set and rearward from the distal tip of the device. Both sets of microwave transducers are positioned within the microwave field. The device of FIG. 6 therefore has an omnidirectional, 360 degree microwave field and a corresponding 360 degree ultrasonic signal output. The use of two spaced sets of ultrasonic transducers can provide more accurate mapping of the surrounding tissue densities. In this embodiment, as in some of the previous embodiments, the inner conductor 50 comprises the first signal connection line or lead between all of the transducers in each set and the signal processing module in signal control and monitoring unit 30 at the proximal end of the device. The second connection line may comprise wires similar to the wires 86 in FIG. 4 which extend through the central lumen 34 of the coaxial conductor and out through the open distal end of inner conductor 50, before bending back over the outer end and extending along the outer surface of inner conductor 50 to connect to the transducers. Alternatively, the second connector wires may extend through the dielectric layer 54 between the inner and outer conductors.

Figure 7A:
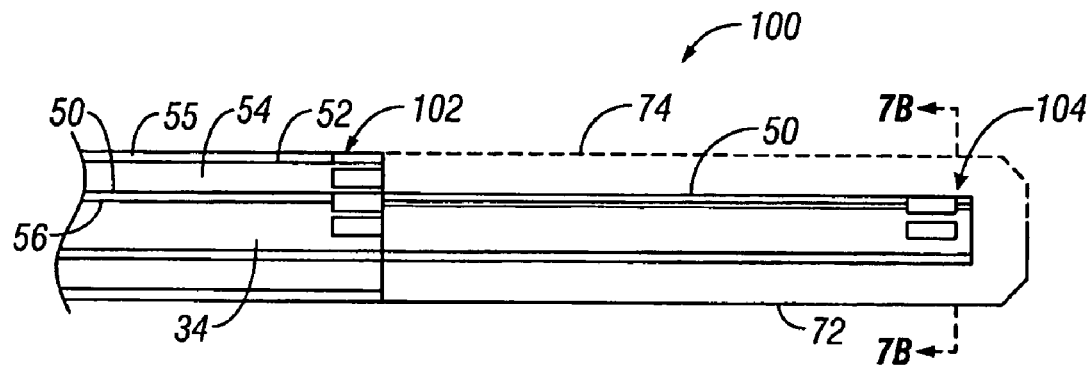
FIG. 7A is a schematically simplified view similar to FIG. 6 of the distal portion of another embodiment of a coaxial cable device having a monopole antenna and a different ultrasonic transducer arrangement.
Figure 7B:
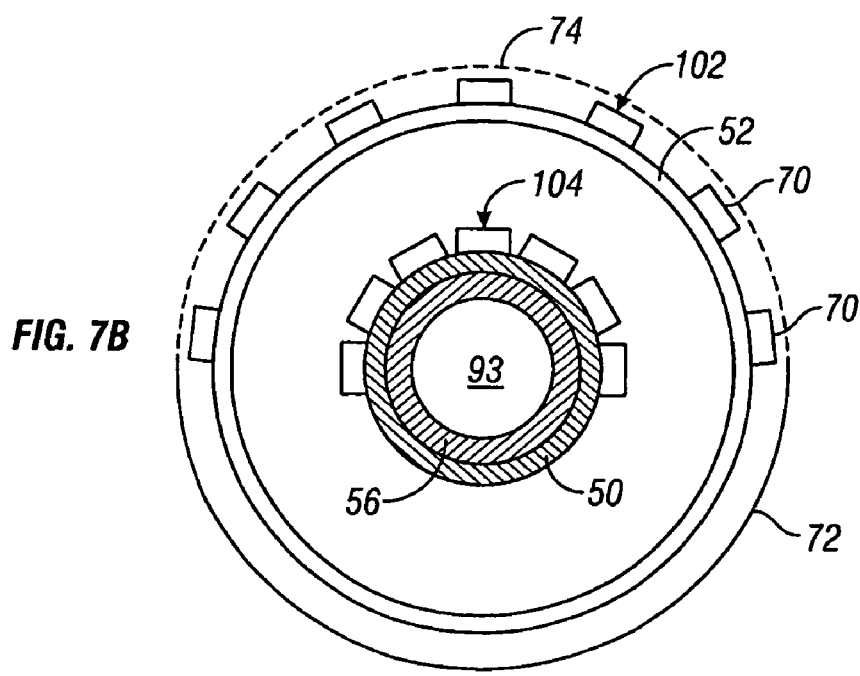
FIG. 7B is a cross-sectional view on the lines 7B-7B of FIG. 7A.

FIGS. 7A and 7B illustrate another embodiment in which the distal portion 100 of ablation device 20 has a monopole RF antenna as in the previous embodiment, along with a modified ultrasonic transducer assembly. Other parts of the coaxial cable or ablation device 20 are identical to parts in one or more of the previous embodiments, and like reference numbers are used for like parts as appropriate. In this embodiment, as in the embodiment of FIG. 2, the outer casing in the distal portion has a first semi-circular portion 72 of microwave absorbing or shielding material, and a second semi-circular portion 74 of microwave and ultrasound transparent dielectric material.

The ultrasonic transducer assembly in this embodiment also comprises spaced sets 102, 104 of transducer elements 70, but the two sets are positioned differently from the previous embodiment. In this embodiment, a first set 102 of ultrasonic transducers is positioned around half of the outer circumference of the outer conductor 52 adjacent the proximal end of the RF antenna, similar to the transducer positioning in FIG. 5, while a second set 104 is positioned around the corresponding half of the outer circumference of the inner conductor 50 close to the distal tip of conductor 50, in a similar position to the transducers in the first embodiment of FIGS. 2A to 2E, with the two sets of transducers facing radially outwardly through the ultrasound transparent aperture or window 74, which in this case has a proximal end adjacent the proximal end of the first transducer set 102. In this case, the inner conductor 50 comprises the first signal connection line or lead from each of the ultrasonic transducers in set 104 to the signal processing and conditioning module at the proximal end of the device, as in some of the previous embodiments. Similarly, outer conductor 52 comprises the first signal connection line or lead from each of the transducers in set 102. Connection wires similar to wires 75 in FIG. 2D and wires 90 in FIG. 5A may be used for the second connection lines.

The distal portion 100 in the embodiment of FIGS. 7A and 7B has a 180 degree microwave and ultrasound aperture, as in the first embodiment, but in this case with two spaced sets or arrays of ultrasonic transducers for improved tissue density mapping. This embodiment can also map a greater area of tissue due to the spacing between the transducer sets, which direct ultrasonic energy radially outwardly through window 74. The distal end portion 100 can be rotated as needed to map all surrounding tissue at the location. Windows 74 of greater or smaller angular extent may be used in other embodiments, with corresponding location of the transducers 70 in radial alignment with the window, depending on the desired angular extent of the microwave and ultrasound signal outputs.

Figure 8A:
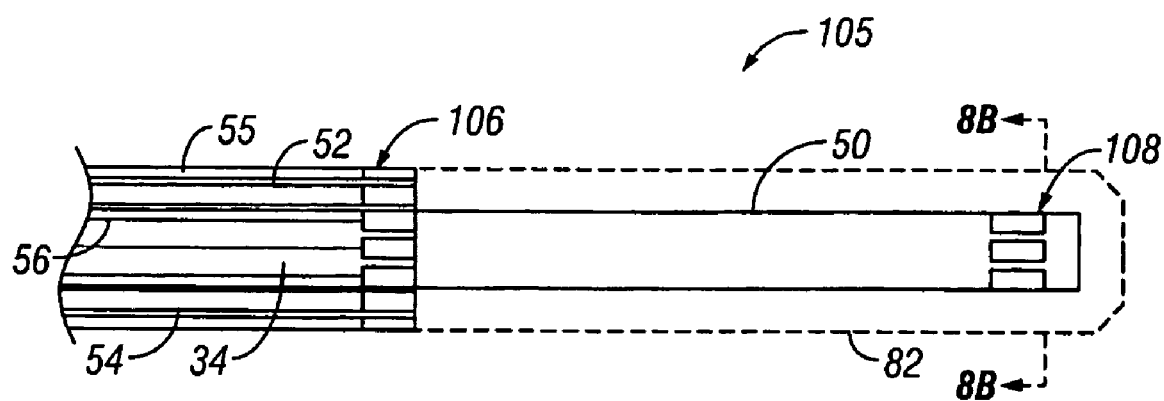
FIG. 8A is a schematically simplified view similar to FIGS. 6A and 7A of the distal portion of another embodiment of a coaxial cable device which is similar to the device of FIGS. 7A and 7B but has a modified outer housing or cover.
Figure 8B:
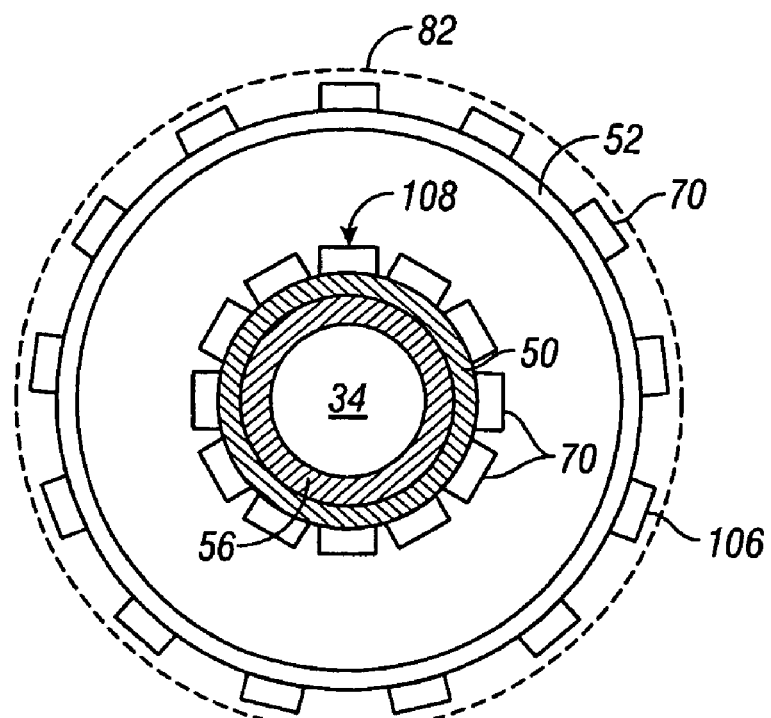
FIG. 8B is a cross-sectional view on the lines 8B-8B of FIG. 8A.

FIGS. 8A and 8B illustrate another embodiment in which the antenna is a monopole antenna. In this embodiment, the distal portion 105 of ablation apparatus 20 has a similar transducer arrangement to the previous embodiment, with two sets or arrays 106, 108 of ultrasonic transducers on the distal ends of the outer conductor 50 and inner conductor 52, respectively. However, in this embodiment, the transducers 70 of each set are spaced around the entire circumference of each conductor, and the part 82 of the outer casing 55 of the device which projects forwardly over the rear set 106 of transducers and up to the distal tip of the device is formed entirely of a material which is transparent to both microwave and ultrasonic signals. This provides a 360 degree microwave and ultrasound aperture. The connection lines between each transducer and the ultrasonic drive signal generating and ultrasonic echo signal processing module 624 may be the same as described above in connection with FIGS. 7A and 7B. Other parts of the coaxial cable or ablation device 20 are identical to parts in one or more of the previous embodiments, and like reference numbers are used for like parts as appropriate.

Figure 9:
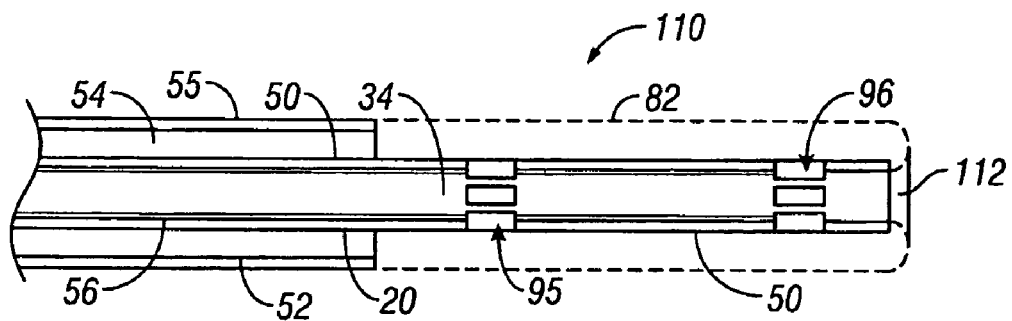
FIG. 9 is a schematically simplified view similar to FIGS. 6A, 7A, and 8A of the distal portion of another embodiment of a coaxial cable device which is similar to the embodiment of FIGS. 6A and 6B but with a central lumen which is open at the forward end of the device.

FIG. 9 illustrates another embodiment in which the antenna is a monopole antenna. The distal portion 110 of the ablation device has two sets 95, 96 of ultrasound transducers on the outer circumference of the inner conductor 50 which are positioned similarly to the two sets in FIG. 6. The transducers in each set are arranged at spaced intervals around the entire circumference of conductor 50, to provide a 360 degree ultrasound signal and 360 ultrasound echo signal monitoring. However, in this case, unlike FIG. 6, the device is open at the distal end of central lumen 34. In other words, casing 55 has an opening 112 at the distal tip 114 which is aligned with the distal end opening of lumen 34. This can allow structures deployed within lumen 34 to be extended forward through end opening 112, such as guide wires, sensors or positioning devices. Apart from the open distal end, the device of FIG. 9 is otherwise identical to the embodiment of FIG. 6, and like reference numbers are used for like parts as appropriate.

Figure 10:
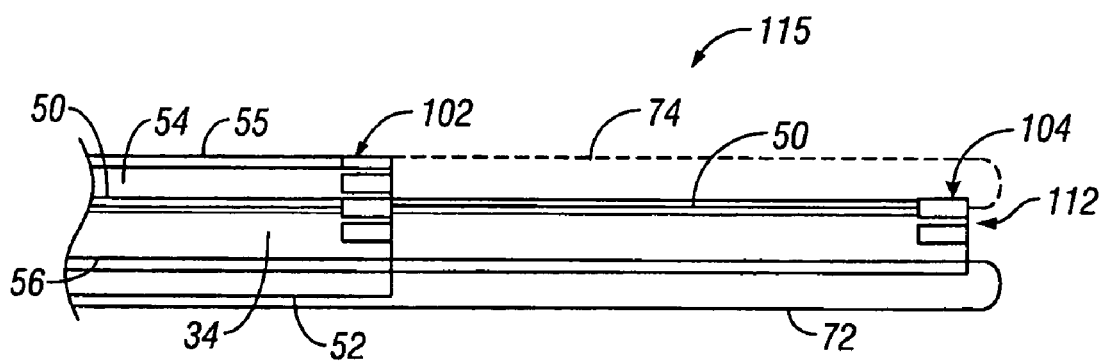
FIG. 10 is a schematically simplified view of a coaxial-cable device similar to the device of FIG. 9 but with a modified ultrasonic transducer and outer cover arrangement similar to that of 7A and 7B.

FIG. 10 illustrates another embodiment which has a distal portion 115 similar to the embodiment of FIGS. 7A and 7B except that the casing 82 extending over the distal portion has a distal end opening 112 as in the previous embodiment. Other parts of this embodiment are identical to the embodiment of FIGS. 7A and 7B, and like reference numerals have been used as appropriate. As in the embodiments of FIGS. 7 to 9, the antenna in this embodiment is a monopole antenna. As in FIGS. 7A and 7B, the outer casing at the distal portion has a 180 degree window 74 of microwave and ultrasound transparent material, and two spaced sets 102, 104 of microwave transducers arrayed around the distal ends of the outer conductor 50 and inner conductor 52, respectively. The transducer sets 102, 104 each extend around half of the circumference of the respective conductor which is radially aligned with the window 74. The remainder or other half 72 of the outer casing is of microwave absorbing or shielding dielectric material, as in FIGS. 2A to 2E and FIGS. 7A and 7B. In alternative embodiments, the window 74 of microwave and ultrasound transparent material may be of greater or smaller angular extent, depending on the size of the tissue area to be treated. The signal connection lines for the two sets 102, 104 may be identical to those described above in connection with FIGS. 7A and 7B.

Figure 11:
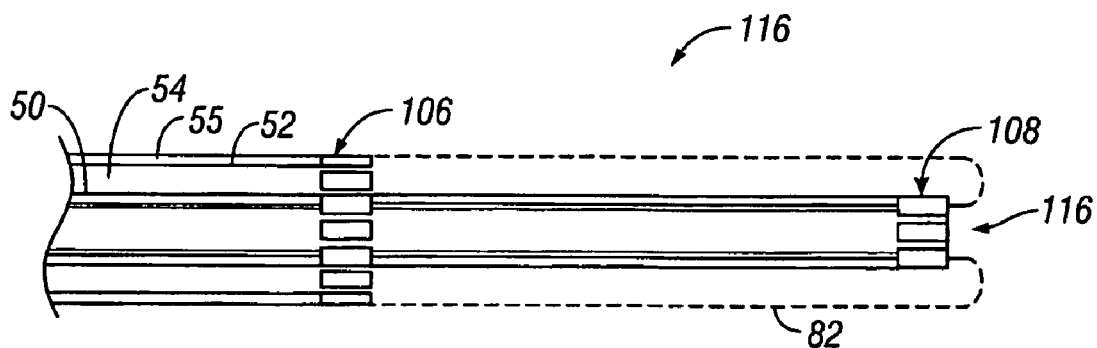
FIG. 11 is a schematically simplified view of a coaxial-cable device similar to the device of FIG. 10 but with a transducer arrangement similar to that of FIGS. 8A and 8B and a modified outer casing arrangement.

FIG. 11 illustrates another embodiment in which the distal portion 116 of the coaxial cable device has an outer casing 82 which is completely transparent to microwaves and ultrasound, as in the embodiments of FIGS. 3, 4, 5, 6, 8 and 9. This embodiment is similar to the embodiment of FIGS. 8A and 8B apart from the fact that the distal end of casing 82 has a central opening or aperture 112 aligned with the open distal end of the central lumen 34, as in the embodiments of FIGS. 9 and 10. As in FIGS. 8A and 8B, this embodiment has an RF antenna comprising a monopole antenna for providing the RF ablation energy, and has two spaced sets 106, 108 of ultrasonic transducers at the distal ends of the outer and inner conductor 52, 50, respectively, which form an array around the entire circumference of the respective conductor, in a similar manner to that illustrated in FIG. 8B.

Each of the foregoing embodiments may incorporate a temperature sensor 76 as illustrated and described above in connection with FIG. 2D, or the temperature sensor may be omitted. Other types of sensors such as EKG electrodes may be incorporated if needed. Although the RF antenna in the embodiments of FIGS. 2 to 5 is a helical coil antenna 26, this antenna may be replaced with a monopole antenna as in FIGS. 6 to 11, or with any other type of RF antenna. Similarly, the monopole antenna of FIGS. 6 to 11 may be replaced with a helical coil antenna 26 as in the embodiments of FIGS. 2 to 5. In any of the foregoing embodiments, the distal tip may have an opening communicating with the central lumen 34 of the coaxial conductor, or may be closed.

The tissue ablation system and method of the above embodiments employs ultrasound transducers disposed radially about at least part of at least one of the conductors of the coaxial conductors, although the transducers may alternatively be located within the lumen 34 or along the surface of the antenna. This arrangement reduces the number of ultrasonic transducer leads required, since the transducers all share at least one conductor with the RF antenna. The ultrasonic echo signals received by the transducers can be processed to determine the approximate borders and depth of a tissue region to be treated, and can be used for positioning of the antenna prior to treatment. The processed signals can also sense the depth of tissue ablation away from the antenna both during and after treatment. During treatment, the ultrasonic sensor outputs may be used to vary the RF ablation signal characteristics. After treatment, the output signals can provide information on the effectiveness of the treatment. Similar configurations of ultrasonic sensors relative to an RF treatment antenna can detect air bubble activity levels in blood and tissue to improve safety and efficacy of the ablation process.

In the embodiments presented herein and in the references incorporated hereto, the inner conductor 50 and outer conductor 52 are configured in a substantially coaxial relationship in which the walls between the conductors define a space 54 extending along at least part of the length of the coaxial cable. As discussed above, the space 54 is configured to interpose dielectricity, which impedes electrical conduction between the inner and outer conductors, which may be effected with the introduction of a vacuum or a dielectric medium. With respect to a dielectric medium, it can comprise a solid dielectric layer which is disposed between the space between the inner conductor 50 and the outer conductor 52. Alternatively, in lieu of the solid dielectric layer, a dielectric fluid medium can be used. Further, where the gaps and recesses are provided as in the various embodiments as exemplified above, one or more solid dielectric layer(s) and a fluid (such as air) can be placed in space 54.

The outer dimensions of the body of the coaxial cable apparatus in each of the above embodiments may be adapted as required to suit the particular medical procedure, as is well known in the medical art. In one embodiment, the device is used to ablate cardiac tissue. However, the device may be used to ablate other types of body tissue in different organs, both internal and external to the body. The tubular body of the coaxial cable apparatus may be generally constructed of a polymer material which is bio-compatible with the body vessel environment.

In each of the above embodiments, the ablation apparatus has an RF antenna which is adapted to receive and radiate electromagnetic energy in order to treat a selected biological tissue site by changing a property of the biological tissue at the site, while one or more ultrasonic sensors or piezoelectric transducers are used to monitor the site. The ultrasonic transducers may be directed radially, axially, or both radially and axially from the distal portion of the apparatus. An example of a suitable spectrum of radio frequency energy for use in tissue ablation is that of the microwave frequency range above 300 MHz. The RF antenna is capable of applying substantially uniformly distributed electromagnetic field energy along the RF antenna in a direction substantially normal to the longitudinal axis of the antenna. The elongated, flexible coaxial cable apparatus is connected to an RF source and ultrasonic drive signal source and control unit at its proximal end and extends to a distal portion at which the RF antenna is mounted. The coaxial cable apparatus in each of the foregoing embodiments has coaxial inner and outer conductors extending from its proximal end and separated by a dielectric medium, and a central lumen or bore inside the inner conductor extends the length of the coaxial cable device and can be used to accommodate conductor wires which are connected to the ultrasonic sensors or transducers, as well as to ECG electrodes, temperature sensors, or the like. In alternative embodiments, a suitable shaping or steering mechanism within the central lumen may also be included for controlling the shape or deflection of the distal end portion of the coaxial cable device in which the RF antenna is located, as described in U.S. Pat. No. 7,004,938, the contents of which are incorporated herein by reference.

Although multiple ultrasonic sensors or transducers are described in each of the above embodiments, alternative embodiments may have a single ultrasound transducer in alignment with a directional microwave antenna to sense depth of tissue ablation away from the antenna. The transducer and antenna may be focused at a narrow radial angle, if a precise, narrow region is to be monitored and treated. Other combinations of microwave antenna and ultrasound transducer may be used by varying the numbers, positions, and arrangement of transducers, providing one, two or more separate arrays of transducers, and varying the antenna length, focus angle, and deflection radius.

The RF energy transmission cable or ablation system described in the above embodiments uses ultrasonic transducers to determine the density contrast of a target tissue site. The density contrast allows identification and characterization of the target tissue. As noted above, one or more ultrasonic sensors or transducers may be installed in the distal portion of the coaxial cable ablation device, adjacent to or in association with the RF antenna. When energized, the ultrasonic transducers impart ultrasonic signals directed to the tissue area or areas of interest. The reflected signals travel at a different velocity from the forward signals, which can be correlated to the density of tissues to which the signals are directed. The density contrast from one tissue location to another may indicate abnormalities such as tumors or other tissue characteristics. In the above embodiments, the inner and outer coaxial cables or conductors define a wave guide by which microwave energy is transmitted from the microwave generator to the antenna, while at the same time the inner cable or outer cable, or both, can be used to connect the ultrasonic transducers or sensors to the ultrasonic drive signal generator.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are, therefore, representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. A hollow coaxial cable apparatus for transmission of radio frequency (RF) energy for the ablation of biological tissues, comprising:
   a hollow coaxial electrical cable having a proximal portion and a distal portion and comprising inner and outer coaxial conductors extending between the proximal portion and the distal portion;
   an outer casing extending over the coaxial conductors from the proximal portion to the distal portion of the cable;
   an RF antenna disposed at the distal portion of the cable which transmits RF energy to a tissue region to be treated;
   a first array of ultrasonic transducers disposed at the distal portion of the cable which directs ultrasonic energy radially outwards from the cable over a predetermined angle to the tissue region, and which detects reflected ultrasonic signals and provides a signal output according to the reflected ultrasonic signals;
   first and second conductive leads extending from the proximal portion of the cable to the ultrasonic transducer, at least the first conductive lead comprising one of the coaxial conductors; and
   the outer casing having a distal portion extending over the RF antenna and ultrasonic transducer array which has a window of ultrasonic and microwave transparent material aligned with the transducer array, the remainder of the distal portion of the casing being of microwave and ultrasound absorbing material.

2. The apparatus of claim 1, further comprising a power supply and control assembly connected to the proximal portion of the cable, the assembly comprising an RF signal generator module which communicates with the RF antenna through the coaxial conductors, and an ultrasonic signal generator and a signal processing module connected to the ultrasonic transducer through the first and second conductive leads, the signal processing module processing output signals from the transducer to provide information on a monitored tissue region.

3. The apparatus of claim 1, wherein the cable has a central lumen extending from the proximal portion to the distal portion of the cable, and the second conductive lead comprises a wire extending from the transducer through the central lumen.

4. The apparatus of claim 1, further comprising a temperature sensor disposed at the distal portion of the cable which detects temperature in the vicinity of a tissue region to be treated.

5. The apparatus of claim 1, wherein the angle is 360 degrees.

6. The apparatus of claim 1, wherein the predetermined angle is 180 degrees.

7. The apparatus of claim 1, wherein the RF antenna has a central longitudinal axis and the transducers are spaced radially about the central axis of the antenna.

8. The apparatus of claim 1, wherein the transducers are disposed on an outer surface of the inner conductor.

9. The apparatus of claim 1, wherein the transducers are disposed on an outer surface of the outer conductor in the vicinity of the proximal portion of the RF antenna.

10. The apparatus of claim 1, further comprising a second array of ultrasonic transducers disposed at the distal portion of the cable and axially spaced from the first array.

11. The apparatus of claim 10, wherein the outer conductor terminates at a distal portion spaced rearwardly from the distal end of the cable and the inner conductor has a portion which projects from the distal portion of the outer conductor, and the first and second arrays are disposed at axially spaced locations on the projecting portion of the inner conductor.

12. The apparatus of claim 10, wherein the outer conductor terminates at a distal portion spaced rearwardly from the distal portion of the cable and the inner conductor has a distal portion which projects from the distal portion of the outer conductor, the first array is located on the distal portion of the outer conductor and the second array is located on the distal portion of the inner conductor.

13. The apparatus of claim 1, wherein the ultrasonic transducer array is a circular array which directs ultrasonic energy radially outwards through an angle of 360 degrees, and the distal portion of the casing which extends over the RF antenna and ultrasonic transducer array is formed of ultrasonic and microwave transparent material.

14. The apparatus of claim 1, wherein the RF antenna has a distal end and a proximal end and is selected from the group consisting of a helical coil antenna, a monopole antenna, and a pair of spaced electrically conductive microstrips.

15. The apparatus of claim 14, wherein the ultrasonic transducer is located adjacent the distal end of the RF antenna.

16. The apparatus of claim 14, wherein the ultrasonic transducer is located adjacent the proximal end of the RF antenna.

17. The apparatus of claim 14, wherein the RF antenna comprises a helical coil antenna which surrounds an area and the ultrasonic transducer is located in the area surrounded by the antenna.

18. The apparatus of claim 1, wherein the cable has a central lumen which is closed at the distal end of the cable.

19. The apparatus of claim 1, wherein the cable has a central lumen which is open at the distal portion of the cable.

20. The apparatus of claim 1, wherein the RF antenna transmits microwave energy at a frequency from approximately 300 Megahertz and up.

21. A radio frequency ablation system, comprising:
an elongated hollow coaxial cable having a proximal portion and a distal portion;
a radio frequency (RF) antenna disposed at the distal portion of the cable which directs RF energy outwardly from the cable for ablation of biological tissue;
inner and outer coaxially aligned, circumferentially spaced, electrically conductive tubular members extending from the proximal portion to the RF antenna;
at least one ultrasonic transducer array disposed on an outer surface of one of the electrically conductive tubular members at the distal portion of the cable, the ultrasonic transducer array being configured to direct ultrasonic signals from the distal portion to a monitored biological tissue region and to receive ultrasonic signals reflected from the monitored biological tissue region;
the ultrasonic transducer array comprises a series of transducers arranged at spaced intervals around an arc co-axial with the RF antenna and subtending a predetermined angle of no more than 180 degrees, whereby the transducers project ultrasonic signals radially outwardly through a predetermined angular range;
a power supply and control assembly connected to the cable, the assembly comprising an RF signal generator module which communicates with the RF antenna through the conductive tubular members, an ultrasonic transducer power supply module which communicates with the ultrasonic transducer array and provides power to generate the ultrasonic signals, and a reflected ultrasonic signal processor module which receives output signals from the ultrasonic transducer array and which processes the output signals to provide information on the tissue in the monitored tissue region; and
the RF antenna being configured to transmit RF energy from the distal end portion of the cable through a predetermined angular range coincident with the angular range of the ultrasonic transducer array.

22. The system of claim 21, wherein the power supply and control assembly further comprises a control module which adjusts the output energy directed from the RF antenna onto a tissue site being treated based on information received from the ultrasonic transducer array.

23. The system of claim 21, further comprising a temperature sensor disposed at the distal portion of the cable which detects temperature in the vicinity of a tissue region during treatment, the power supply and control assembly further comprising a temperature output module which receives detected temperature signals from the temperature sensor and compares the output signals with a preset temperature setting, and a control module which adjusts the RF output energy from the RF antenna based on the detected temperature.

24. The system of claim 23, wherein the control module adjusts the RF output energy based on both the detected temperature and the reflected ultrasonic signals received by the ultrasonic sensor assembly.

25. The system of claim 21, wherein the ultrasonic transducer array is unidirectional.

26. The apparatus of claim 1, wherein the ultrasonic transducer array comprises a series of transducers arranged at spaced intervals around an arc co-axial with the RF antenna and subtending a predetermined angle of no more than 180 degrees.

27. The system of claim 21, further comprising an outer casing having a distal portion extending over at least the RF antenna and ultrasonic transducer array which has a window of ultrasonic and microwave transparent material aligned with the transducer array and extending around said predetermined angle, the remainder of the distal portion of the casing being of microwave and ultrasound absorbing material.

* * * * *